United States Patent
Fiore

(10) Patent No.: US 11,771,418 B2
(45) Date of Patent: Oct. 3, 2023

(54) COMBINATION FORCEPS

(71) Applicant: Joseph Paul Fiore, San Diego, CA (US)

(72) Inventor: Joseph Paul Fiore, San Diego, CA (US)

(*) Notice: Subject to any disclaimer, the term of this patent is extended or adjusted under 35 U.S.C. 154(b) by 348 days.

(21) Appl. No.: 17/142,146

(22) Filed: Jan. 5, 2021

(65) Prior Publication Data
US 2022/0211366 A1 Jul. 7, 2022

(51) Int. Cl.
*A61B 17/04* (2006.01)
*A61B 17/28* (2006.01)

(52) U.S. Cl.
CPC .......... *A61B 17/0483* (2013.01); *A61B 17/28* (2013.01)

(58) Field of Classification Search
CPC ... A61B 17/0483; A61B 17/28; A61B 17/062; A61B 2017/303
See application file for complete search history.

(56) References Cited

U.S. PATENT DOCUMENTS

| | | | |
|---|---|---|---|
| 5,449,374 A * | 9/1995 | Dunn | A61B 17/2812 606/208 |
| 6,863,679 B1 * | 3/2005 | Aaron | A61B 17/30 606/210 |
| 7,641,248 B2 * | 1/2010 | Cho | B25B 9/02 294/99.2 |
| 7,682,372 B2 * | 3/2010 | Peterson | A61B 17/04 606/211 |
| 10,188,416 B2 * | 1/2019 | Alshemari | A61B 17/30 |

FOREIGN PATENT DOCUMENTS

WO WO-2019099660 A1 * 5/2019

* cited by examiner

*Primary Examiner* — Julian W Woo

(57) ABSTRACT

Surgical instruments and methods for using and manufacturing the same are provided. The surgical instrument includes a combination of serrated forceps and non-serrated forceps, the serrated forceps and the non-serrated forceps being operable independently of each other. A method of using the instrument includes using the serrated forceps of the instrument to grasp a tissue and using the non-serrated forceps of the instrument to pull a surgical needle through the tissue. A method of manufacturing the surgical instrument includes manufacturing serrated forceps and non-serrated forceps, such that the inner shanks of the serrated and the non-serrated forceps form a central shank, wherein the surgical instrument operates in a way that pushing the outer shank of the serrated forceps toward the central shank of the instrument engages the serrated forceps of the instrument, and pushing the outer shank of the nonserrated forceps toward the central shank of the instrument engages the non-serrated forceps of the instrument.

12 Claims, 7 Drawing Sheets

COMBINATION FORCEPS

BACKGROUND OF THE INVENTION

Field of the Invention

This disclosure pertains to the field of surgical instruments. More particularly, this disclosure pertains to surgical forceps and methods of manufacturing and using the same in surgery upon tissue.

Background

Surgical forceps are used to grasp and manipulate objects, such as tissue, surgical needles or suture threads. Among other uses, serrated forceps may be used to grasp and position tissue. Among other uses, non-serrated forceps may be used to pick up or manipulate surgical needles. Many surgical procedures require the operator to switch back and forth between stand-alone serrated and non-serrated forceps. Sequencing between two types of stand-alone forceps during an operation is time-consuming, increases the risk of contaminating the sterile forceps and the operating field, and often requires the extra hands of an assistant, which may not be possible in many situations.

There is, therefore; a need for combination forceps that overcome the above deficiencies of existing forceps.

SUMMARY

The disclosed embodiments provide for surgical instruments and methods for using and manufacturing the same. In one aspect, the instrument comprises serrated forceps and non-serrated forceps, the serrated forceps and the non-serrated forceps being at least partially connected side-by-side along the inner shanks of the serrated and the non-serrated forceps.

In another aspect, a method of using the surgical instrument comprises using the serrated forceps to grasp a tissue, running a surgical needle through the tissue, releasing the tissue and using the non-serrated forceps to pull the needle out through the tissue.

In yet another aspect, a method of manufacturing a surgical instrument comprises manufacturing serrated forceps, the serrated forceps having an inner shank and an outer shank; manufacturing a non-serrated forceps, the non-serrated forceps having an inner shank and an outer shank; and connecting the serrated and the non-serrated forceps side-by-side at least partially along the inner shanks of the serrated and the non-serrated forceps, thereby forming a central shank.

In another aspect, the surgical instrument may be used in a way such that pushing the outer shank of the serrated forceps toward the central shank of the instrument engages the serrated forceps of the instrument and pushing the outer shank of the non-serrated forceps toward the central shank of the instrument engages the non-serrated forceps of the instrument.

DETAILED DESCRIPTION

Figure 1:
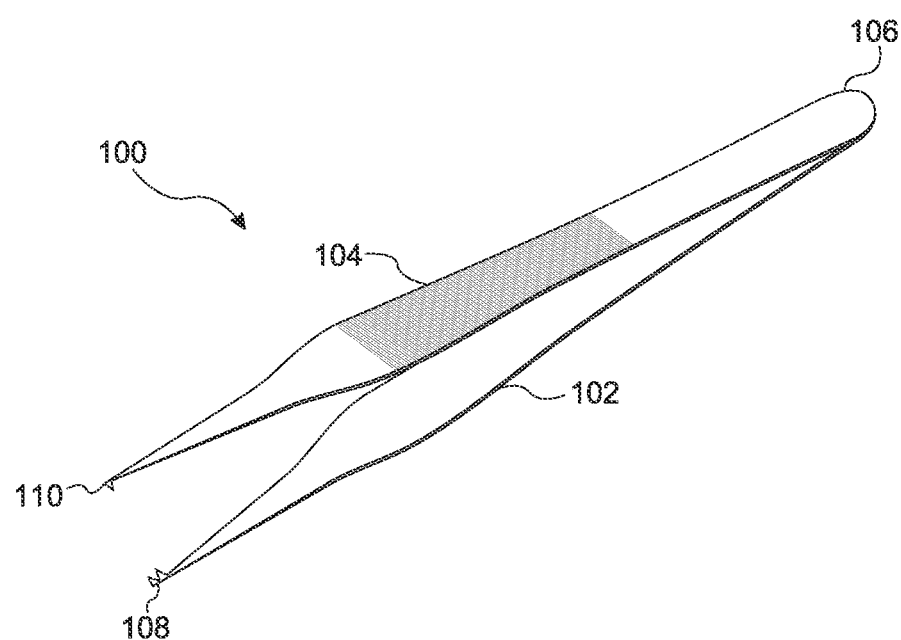
FIG. 1 shows a pair of serrated forceps.

As shown in FIG. 1, the forceps 100 comprises a pair of shanks, also referred to as prongs, arms or legs, 102 and 104, which may be connected at a handle portion 106. Shank 102 has distal end 108, and shank 104 has a distal end 110. When the shanks 102 and 104 are pressed toward each other, e.g., by a thumb and an index finger, the forceps 100 would come to a closed or engaged position. The interior surfaces of distal ends 108 and 110 may be serrated. As shown in FIG. 1, according to one embodiment, the inner surfaces of the distal ends 108 and 110 comprise a teeth combination, such as two teeth on one side meshing with a single tooth on the opposing, that engage when the shanks 102 and 104 are pressed or moved toward each other. Other embodiments of teeth arrangements, in terms of shape, number, and layout of the teeth, are also within the scope of the disclosed embodiments. Serrated forceps may be safely used on tissue, as teeth may damage tissue less than a smooth surface (non-serrated) because a practitioner can grasp the tissue with less overall pressure.

Forceps 100 may be conveniently used for grasping, holding or manipulating tissue in various surgical procedures in clinical, pathology, or research settings, for example. The term tissue comprises skin tissue, muscle tissue, nerve tissue and the like. The serrated tips of the distal ends 108 and 110 of the forceps 100 help in firmly holding or grasping tissue between the shanks 102 and 104 when a practitioner attempts to move, turn, open, close, hold or evert tissue, for example.

In another embodiment, the forceps 100 may have other forms of tips that help grasp tissue firmly. Other forms of tips that provide a firm grasp of the tissue may be cupped, ringed, grooved, diamond dusted, curved, cross-hatched, or angled. In yet another embodiment, the tips of the forceps 100 may comprise a retracting hook which may be moved axially in and out of the forceps 100 to pinch or hold tissue. In another example, the tip of the forceps 100 may comprise a suction tube which may be used to hold tissue when vacuum is applied to the suction tube. In yet another example, the distal end of the forceps 100 may be in the form of a pliers, which may be used to clamp tissue.

Figure 2:
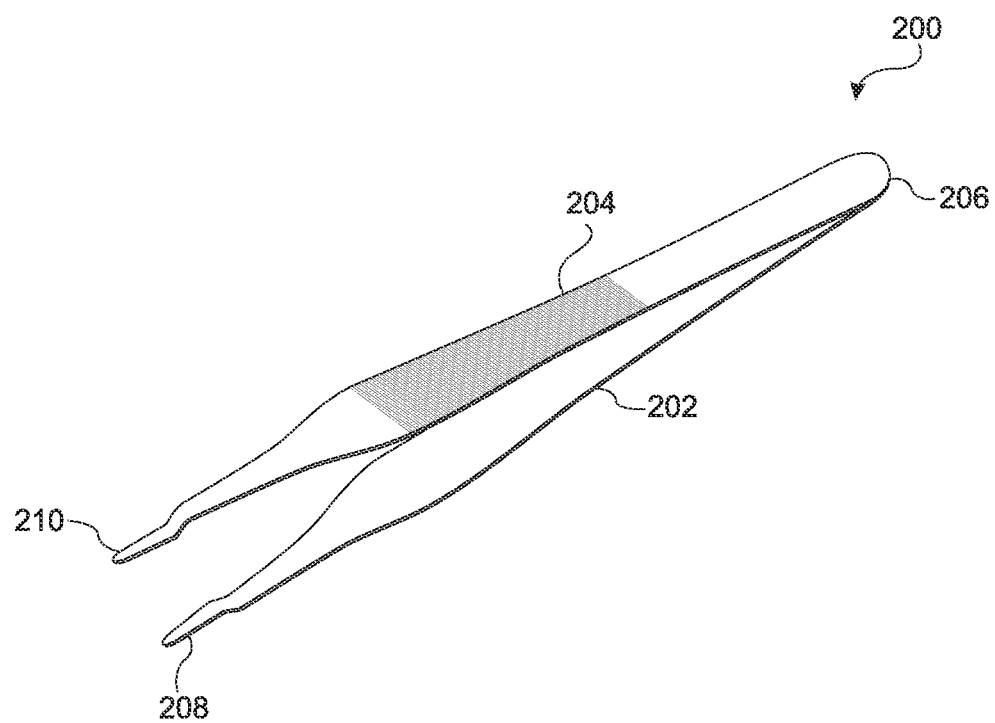
FIG. 2 shows a pair of non-serrated forceps.

FIG. 2 shows forceps 200 which comprises a pair of diverging shanks 202 and 204, which may be connected at a handle portion 206. Shank 202 has a distal end 208, and shank 204 has a distal end 210. In one embodiment, the inner surfaces of the distal ends 208 and 210 are non-serrated, smooth or flat, and distal ends 208 and 210 are designed to come to a tight surface contact. When the shanks 202 and 204 are pressed toward each other, e.g., by a thumb and an index finger, the forceps 200 would come to a tightly closed or engaged position, such that the distal ends 208 and 210 form an air-tight-surface contact. Therefore, the non-serrated forceps 200 may be conveniently used to firmly an unmovably grasp hard objects, such as surgical needles, suture threads, dressings or similar objects. For example, A practitioner may use the non-serrated forceps 200 as a needle holder and unmovably grasp a surgical needle and controllably manipulate the needle, e.g., pull the needle out of a tissue without losing control, whilst holding a metal needle within the metal-to-metal contact of the distal ends 208 and 210 of the forceps 200, while the surgical needle may be slippery due to being covered with blood, fat or the like.

In another example, a practitioner may use the non-serrated forceps 200 conveniently for grasping a suture thread, or other similarly thin objects used in operating on tissue, and unmovably grasp and controllably manipulate the suture thread, e.g., pull the suture thread out of a tissue without losing control, while tightly holding the suture thread within the surface-contact of the distal ends 208 and 210 of the forceps 200, even when the surgical suture is covered with blood, fat or the like.

Figure 3:
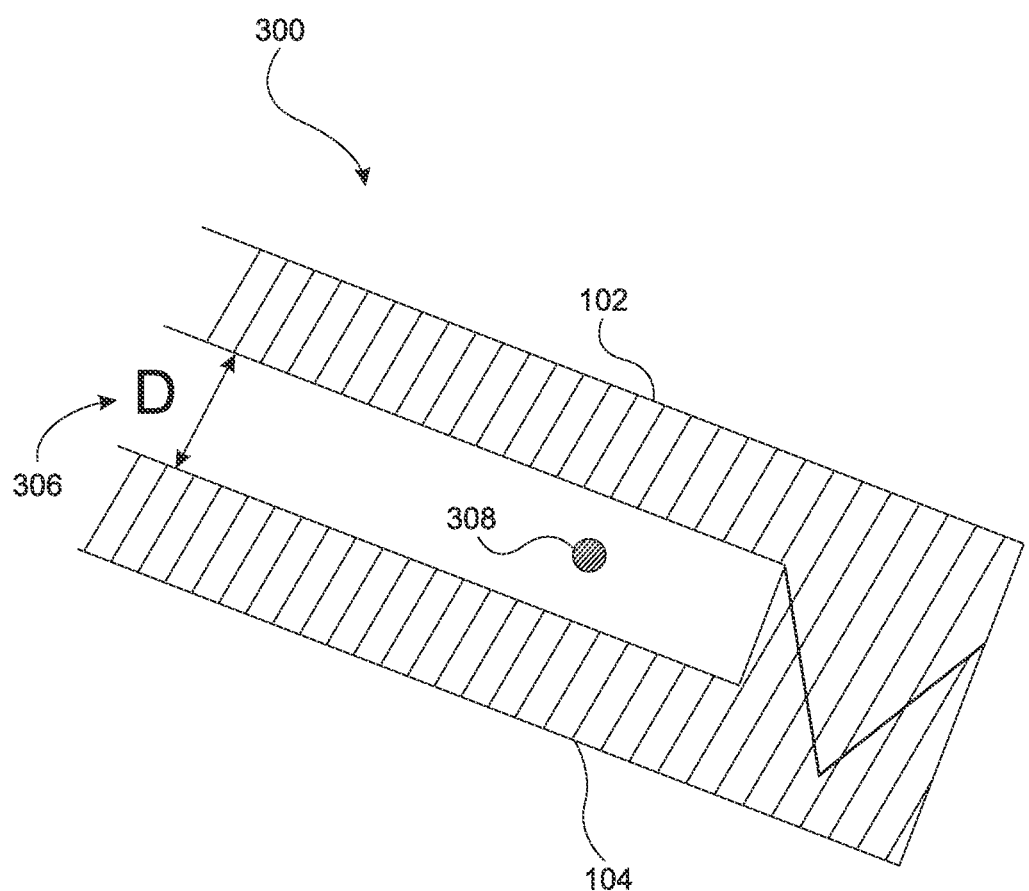
FIG. 3 shows a pair of serrated forceps in fully engaged position.

FIG. 3 show a serrated forceps 300 in a most tightly closed position. As illustrated, there is a space or gap "D" 306 between the shanks 102 and 104, even when the tips of the shanks are tightly touching each other. The structure of the serrated forceps 300 is such that the part of the shank 102 proximal to the teeth of the serrated forceps 300 may not come tightly in touch with the proximal portion of the opposite shank 104, thus; creating the gap "D" 306 between the shanks 102 and 104 of the forceps 300. As such, only the thickest, largest suturing needles with enough girth allow for being grasped within the jaws of the serrated forceps 300. In addition, grasping a metal suturing needle with the metal teeth of serrated forceps is awkward, because the suturing needle tends to slip off the sharp edges of the metal teeth. This is especially the case when the suturing needle becomes covered with blood or fat, as it inevitably does.

Figure 4:
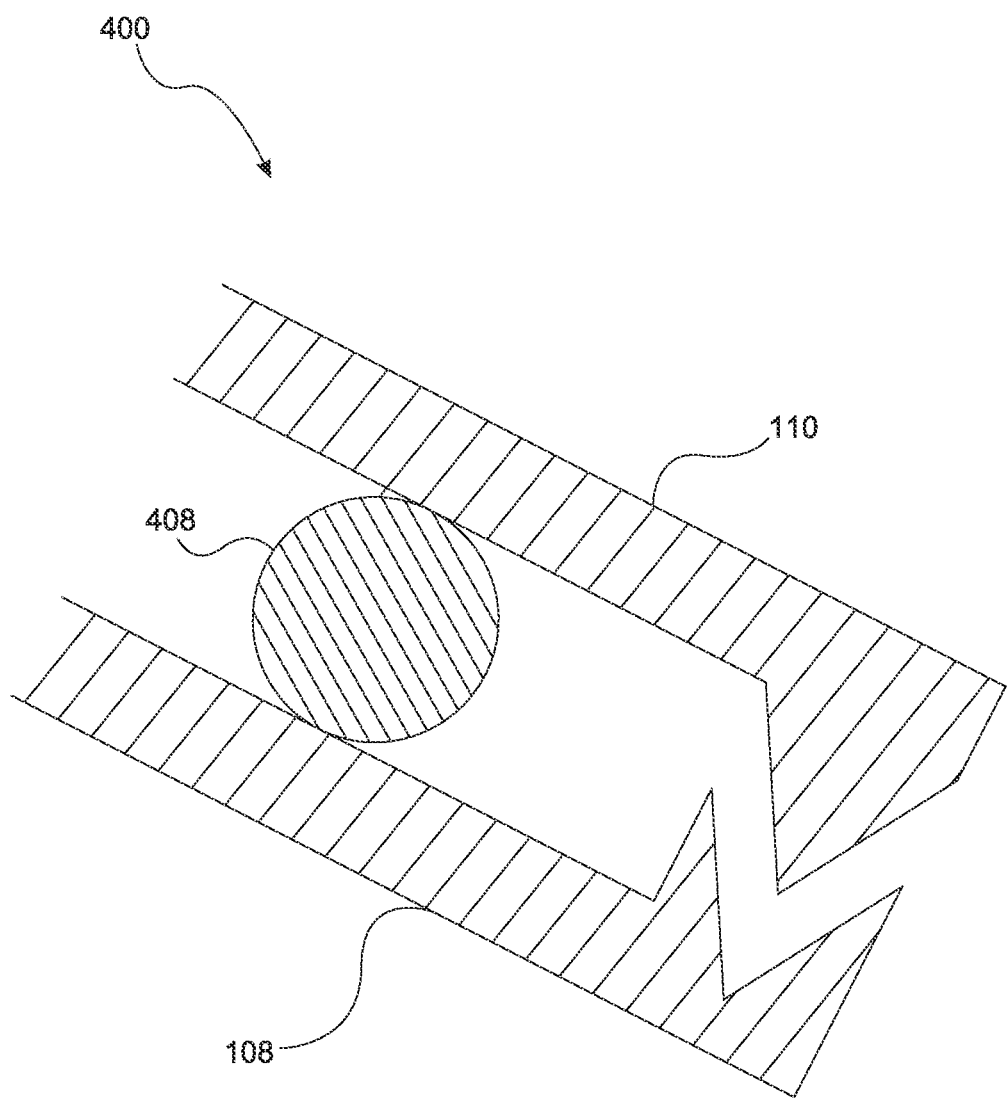
FIG. 4 shows a pair of serrated forceps in partially engaged position.

Therefore, the serrated forceps 300, even in its most tightly closed position as shown in FIG. 3, is not suitable for firmly and unmovably grasping a thin object 308, e.g., a surgical needle or suture thread, with diameter or thickness smaller than the gap "D" 306 created between the shanks 102 and 104 of the closed serrated forceps 300. In addition, the non-flat portion of the distal end of the serrated forceps 300 is not useful for grasping metal or hard objects, thus; reducing the effective grasping area of the serrated forceps 300. As shown in FIG. 4, the serrated forceps 400 would be functional and suitable for grasping only objects 408 with thickness or diameter larger than the gap "D" 306 created between the shanks 102 and 104 of the closed serrated forceps 300, as shown in FIG. 3.

Figure 5:
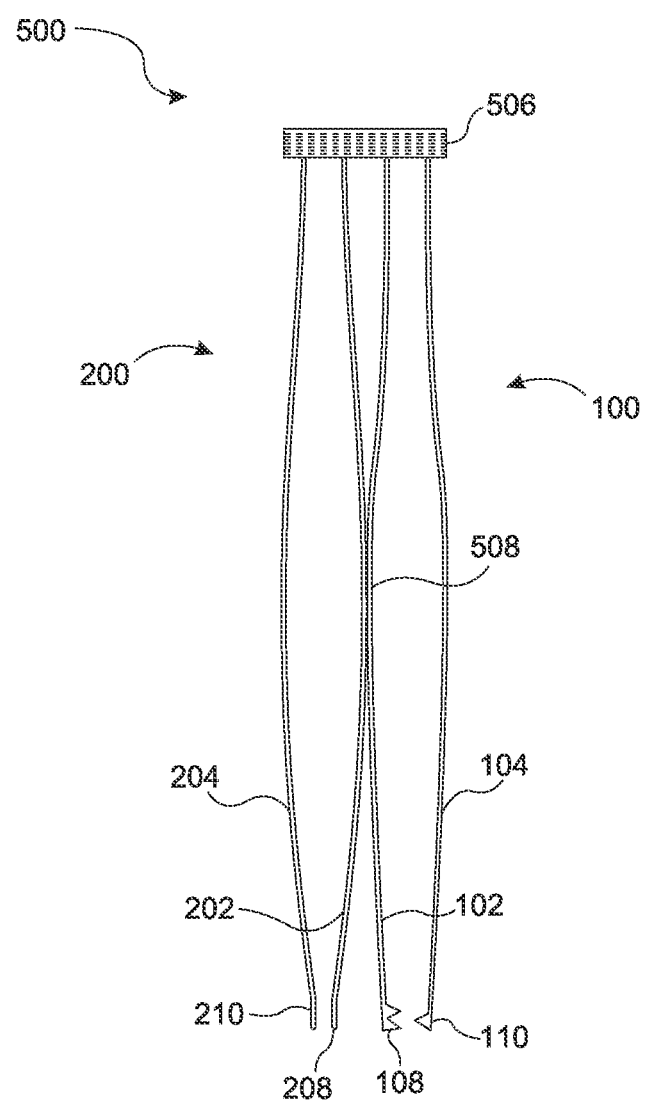
FIG. 5 shows a combination forceps, according to one embodiment.
Figure 6:
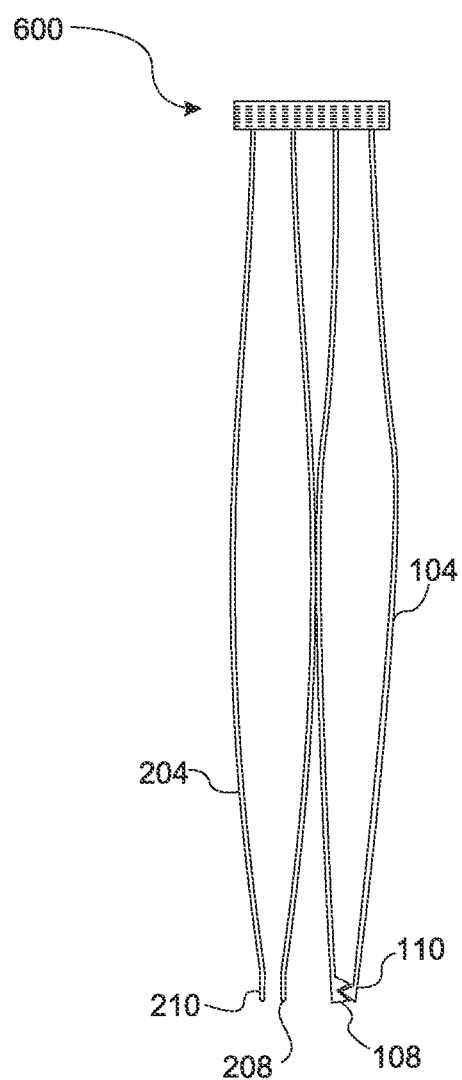
FIG. 6 shows the combination forceps of FIG. 5, wherein the serrated forceps is engaged.

In one embodiment, a combination forceps may include at least one forceps from each of the groups of forceps 100 and 200, which may be manufactured as one piece, or individual forceps may be assembled, connected, fused or tied together. In FIG. 5, according to one embodiment, a serrated forceps 100 and a non-serrated forceps 200 are positioned side-by-side and connected at a handle portion 506. The two forceps 100 and 200 may also be connected or fused at a contact area 508 along the inner shanks 102 and 202, thereby, forming a central shank with the serrated shank 102 on one side and the non-serrated shank 202 on the other side of the central shank. When a practitioner pushes or moves the shank 104 toward the central shank, e.g., by an index finger while anchoring another finger and a thumb on the central shank, the serrated forceps of the instrument 500 will come to the engaged position, as shown by the instrument 600 in FIG. 6. Therefore, in serrated forceps mode of operation, the practitioner may use the combination forceps instrument 500 to firmly grasp and manipulate tissue, as explained above in connection with FIG. 1.

Figure 7:
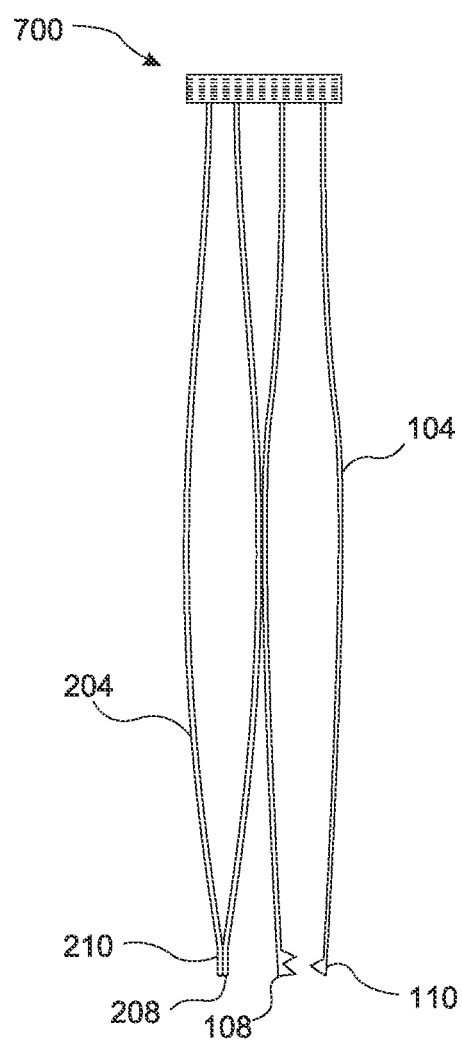
FIG. 7 shows the combination forceps of FIG. 5, wherein the non-serrated forceps is engaged.

Similarly, when a practitioner pushes or moves the shank 204 toward the central shank, e.g., by an index finger, while anchoring another finger and a thumb on the central shank, the non-serrated forceps of the instrument 500 will come to the closed or engaged position, as shown by the instrument 700 in FIG. 7. Therefore, in non-serrated mode of operation, the practitioner may use the combination forceps instrument 500 to firmly and unmovably grasp a hard object within the surface contact of the distal ends 208 and 210, and unmovably manipulate the object, e.g., pull out a surgical needle or suture thread out of tissue, as explained above in connection with FIG. 2.

A practitioner may use the combination forceps instrument 500, independently, to either firmly and conveniently grasp or manipulate tissue, as serrated forceps; or firmly and unmovably grasp and control movement of a surgical needle through the tissue, as non-serrated forceps; thereby eliminating the need for swapping one type of stand-alone forceps for another type of stand-alone forceps, thereby advantageously resulting in reducing the risk of contamination, eliminating extra hands for swapping one type of forceps for another type of forceps, and; thus, reducing time and energy of surgical, pathology, or research operations.

Other multi-forceps arrangements comprising different number of different types of forceps currently known or designed in future for similar or different applications are within the scope of the disclosed embodiments. For example, multiple forceps of varying types of forceps may be assembled in a single instrument in a linear, radial or other arrangements. Multiple-forceps instruments configured for other configurations of a practitioner's hand and fingers in relation to the operation of the instruments 500, 600, and 700 are also within the scope of the present disclosure.

Accordingly, it is to be understood that the embodiments herein described are merely illustrative of the design and application of the principles of the claimed subject matter. Reference herein to details of the illustrated embodiments is not intended to limit the scope of the claims.

What is claimed is:

1. An instrument, comprising:
a serrated forceps that is configured to grasp a tissue; and
a non-serrated forceps that is configured to control movement of an object through the tissue,
wherein the serrated forceps comprises an inner shank and an outer shank, and the non-serrated forceps comprises an inner shank and an outer shank, and each of the inner and outer shanks of the serrated and non-serrated forceps comprises a proximal end and a distal end,
wherein the inner shanks of the serrated and non-serrated forceps are positioned side-by-side, and
wherein the proximal ends of the inner and outer shanks of the serrated forceps and the non-serrated forceps are spaced apart from one another and are each fused to a handle portion.

2. The instrument of claim 1, wherein the non-serrated forceps further is configured to grasp and controllably pull a surgical needle out of the tissue.

3. The instrument of claim 1, wherein the non-serrated forceps further is configured to grasp and controllably insert a surgical needle through the tissue.

4. The instrument of claim 1, wherein the serrated and non-serrated forceps are operable independently.

5. The instrument of claim 1, wherein the non-serrated forceps further comprises a flat surface-contact tip.

6. The instrument of claim 1, wherein the inner shanks of the serrated and non-serrated forceps are fused partially together at a contact area along the inner shanks of the serrated and non-serrated forceps.

7. A method of operating an instrument, the instrument comprising a serrated forceps and a non-serrated forceps being operable independently, wherein the serrated and the non-serrated forceps each comprises an inner shank and an outer shank, wherein each of the inner and outer shanks of the serrated and non-serrated forceps comprises a proximal end and a distal end, wherein the inner shanks of the serrated and non-serrated forceps are positioned side-by-side, and wherein the proximal ends of the inner and outer shanks of the serrated forceps and the non-serrated forceps are each fused to a handle portion and are spaced apart from one another;

the method comprising:
using the serrated forceps to grasp a tissue; and
using the non-serrated forceps to control movement of an object through the tissue.

8. The method of claim 7, wherein said using the non-serrated forceps comprises grasping and controllably pulling a surgical needle out of the tissue.

9. The method of claim 8, wherein said using the non-serrated forceps comprises grasping and controllably inserting a surgical needle through the tissue.

10. The method of claim 7, wherein the inner shanks of the serrated and the non-serrated forceps are fused partially together at a contact area.

11. A surgical instrument, comprising:
a serrated forceps, the serrated forceps having an inner shank and an outer shank; and
a non-serrated forceps, the non-serrated forceps having an inner shank and an outer shank; wherein each of the inner and outer shanks of the serrated and non-serrated forceps comprises a proximal end and a distal end,
wherein, the serrated and the non-serrated forceps are positioned side-by-side and fused partially together at a contact area along the inner shanks of the serrated and the non-serrated forceps,
wherein, pushing the outer shank of the serrated forceps inward causes engagement with the inner shank of the serrated forceps of the instrument, and pushing the outer shank of the non-serrated forceps inward causes engagement with the inner shank of the non-serrated forceps of the instrument, and wherein the proximal ends of the inner and outer shanks of the serrated and non-serrated forceps are spaced apart from one another.

12. The instrument of claim 11, wherein the proximal ends of the inner and outer shanks of the serrated forceps and the non-serrated forceps are each fused to a handle portion.

\* \* \* \* \*